US009907926B2

(12) United States Patent
Allum

(10) Patent No.: US 9,907,926 B2
(45) Date of Patent: Mar. 6, 2018

(54) OXYGEN CONCENTRATOR FOR MECHANICAL VENTILATION

(71) Applicant: SILVERBOW DEVELOPMENT, LLC, San Ramon, CA (US)

(72) Inventor: Todd Allum, Livermore, CA (US)

(73) Assignee: SILVERBOW DEVELOPMENT, LLC., San Ramon, CA (US)

( * ) Notice: Subject to any disclaimer, the term of this patent is extended or adjusted under 35 U.S.C. 154(b) by 616 days.

(21) Appl. No.: 14/516,468

(22) Filed: Oct. 16, 2014

(65) Prior Publication Data

US 2015/0107585 A1   Apr. 23, 2015

Related U.S. Application Data

(60) Provisional application No. 61/893,022, filed on Oct. 18, 2013.

(51) Int. Cl.
*A61M 16/10* (2006.01)
*A61M 16/00* (2006.01)
(Continued)

(52) U.S. Cl.
CPC ...... *A61M 16/101* (2014.02); *A61M 16/0672* (2014.02); *A61M 16/0816* (2013.01);
(Continued)

(58) Field of Classification Search
CPC ............ A61M 16/0063; A61M 16/101; B01D 53/047; B01D 53/0476; B01D 53/053;
(Continued)

(56) References Cited

U.S. PATENT DOCUMENTS 2,896,971 A * 7/1959 Kolar ..................... A62B 9/04
251/149.7
4,636,226 A * 1/1987 Canfora ................. B01D 53/04
95/138
(Continued)

FOREIGN PATENT DOCUMENTS

WO   2007130377 A2   11/2007

OTHER PUBLICATIONS

International Search Report and Written Opinion for International Application No. PCT/US2014/061043 dated Dec. 31, 2014.
(Continued)

*Primary Examiner* — (Jackie) Tan-Uyen T Ho
*Assistant Examiner* — Joseph D Boecker
(74) *Attorney, Agent, or Firm* — Artegis Law Group, LLP

(57) ABSTRACT

An oxygen concentrator is configured to provide oxygen at either lower pressures or higher pressures. When providing low pressure oxygen, the disclosed oxygen concentrator may be used with a conventional, low pressure oxygen delivery device, such as an oxygen cannula or mask, that is configured to deliver oxygen at approximate source pressures of 5 psig to 8 psig. When providing high pressure oxygen, the disclosed oxygen concentrator may be used with a high pressure oxygen delivery device, such as a low profile nasal cannula, that is configured to deliver oxygen at higher pressures. The disclosed oxygen concentrator is configured to automatically select whether low pressure oxygen or high pressure oxygen should be output to the user based on the type of connector used to couple a delivery device thereto, or based on characteristics of the delivery device itself.

23 Claims, 7 Drawing Sheets

(51) Int. Cl.
*A61M 16/06* (2006.01)
*A61M 16/08* (2006.01)
*A61M 16/20* (2006.01)
*B01D 53/04* (2006.01)
*B01D 53/047* (2006.01)

(52) U.S. Cl.
CPC ....... *A61M 16/209* (2014.02); *B01D 53/0446* (2013.01); *A61M 16/0063* (2014.02); *A61M 16/105* (2013.01); *A61M 2016/0027* (2013.01); *A61M 2016/1025* (2013.01); *A61M 2202/0208* (2013.01); *A61M 2202/0266* (2013.01); *A61M 2205/3327* (2013.01); *A61M 2205/3334* (2013.01); *A61M 2205/75* (2013.01); *B01D 53/047* (2013.01); *B01D 2253/108* (2013.01); *B01D 2256/12* (2013.01); *B01D 2257/102* (2013.01); *B01D 2259/402* (2013.01); *B01D 2259/4533* (2013.01)

(58) Field of Classification Search
CPC ...... B01D 2259/402; B01D 2259/4533; B01D 2256/12; B01D 2257/102; A62B 7/02; A62B 7/14
See application file for complete search history.

(56) References Cited

U.S. PATENT DOCUMENTS

| | | | |
|---|---|---|---|
| 4,997,465 A | | 3/1991 | Stanford |
| 5,071,453 A | * | 12/1991 | Hradek ............... A61M 16/101 |
| | | | 95/19 |
| 5,354,361 A | * | 10/1994 | Coffield ............... B01D 53/047 |
| | | | 95/103 |
| 6,394,088 B1 | * | 5/2002 | Frye ...................... A61M 16/20 |
| | | | 128/204.23 |
| 2003/0005928 A1 | | 1/2003 | Appel et al. |
| 2005/0161043 A1 | * | 7/2005 | Whitley ............. B01D 53/0473 |
| | | | 128/205.18 |
| 2006/0157058 A1 | * | 7/2006 | Aylsworth ........... A61M 16/10 |
| | | | 128/204.23 |
| 2006/0174873 A1 | | 8/2006 | Jagger et al. |
| 2007/0084342 A1 | * | 4/2007 | Hunter .................. B01D 53/04 |
| | | | 95/130 |
| 2007/0214955 A1 | * | 9/2007 | Aylsworth ......... B01D 53/0454 |
| | | | 95/19 |
| 2008/0118373 A1 | | 5/2008 | Richey et al. |
| 2014/0202461 A1 | * | 7/2014 | Goertzen ............. A61M 16/10 |
| | | | 128/202.26 |

OTHER PUBLICATIONS

Extended European Search Report for Application No. EP 14853683.2 dated Jun. 13, 2017, 8 pages.

* cited by examiner

OXYGEN CONCENTRATOR FOR MECHANICAL VENTILATION

CROSS-REFERENCE TO RELATED APPLICATIONS

This application claims the priority benefit of the U.S. provisional patent application titled, "Oxygen Concentrator for Mechanical Ventilation," filed on Oct. 18, 2013 and having Ser. No. 61/893,022. The subject matter of this related application is hereby incorporated herein by reference.

BACKGROUND OF THE INVENTION

Field of the Invention

Embodiments of the present invention relate generally to concentrators, and, more specifically, to an oxygen concentrator for mechanical ventilation.

Description of the Related Art

An oxygen concentrator is a mechanical device that filters nitrogen out of atmospheric air to produce fluid with a higher concentration of oxygen. The oxygen is delivered to a user via a delivery device, such as an oxygen mask or nasal cannula. Conventional oxygen concentrators output oxygen to users at pressures between 5 and 8 pounds per square inch gage (psig). Generally, during operation, such oxygen concentrators rely on one or more compression pumps that force air through a zeolitic sieve bed that adsorbs nitrogen. Pressurized oxygen is driven out of the zeolitic sieve bed and is stored in a product tank for delivery to the user.

One drawback of conventional oxygen concentrators is that certain types of delivery devices, such as smaller varieties of nasal cannula, require higher pressures in order to ensure effective oxygen delivery to the user. Under normal operating conditions, a conventional oxygen concentrator cannot provide high pressures, and so delivery devices designed for those high pressures cannot be used with conventional oxygen concentrators, thereby limiting usability.

One solution to this problem is to increase the rate with which the compression pumps operate, thereby increasing the pressure of oxygen within the product tank. However, this technique is generally problematic because increasing pump speed may cause undue mechanical fatigue, thereby reducing the overall lifetime of the oxygen concentrator. In addition, increasing pump speed generally increases power consumption. With portable oxygen concentrators that rely on battery power, an increase in power consumption may result in a corresponding increase in battery size, which reduces portability, or a decrease in operating time, which limits usability.

As the foregoing illustrates, what is needed in the art is an oxygen concentrator that more effectively delivers relative to conventional oxygen concentrators.

SUMMARY OF THE INVENTION

One embodiment of the present invention sets forth a system for delivering oxygen to a user, including an oxygen concentrator that includes a first pump configured to pump atmospheric air through a first sieve bed at a first pressure to generate a first quantity of oxygen, a second pump configured to evacuate nitrogen from a second sieve bed at a second pressure, a pressure amplifier configured to pressurize the first quantity of oxygen to a third pressure to produce pressurized oxygen based on a pressure differential between the first pressure and the second pressure, a product tank coupled to the pressure amplifier and configured to store the pressurized oxygen for delivery to the user, and a user connection switch, configured to deliver the pressurized oxygen to the user via a delivery device.

One advantage of the techniques set forth herein is that users may obtain oxygen at a range of different pressures corresponding to different types of oxygen delivery devices. Accordingly, the user may rely upon conventional low pressure delivery devices or, alternatively, high pressure oxygen delivery devices, depending on user preference.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

In the following description, numerous specific details are set forth to provide a more thorough understanding of the present invention. However, it will be apparent to one of skill in the art that the present invention may be practiced without one or more of these specific details. In other instances, well-known features have not been described in order to avoid obscuring the present invention.

As described in greater detail herein, an oxygen concentrator is configured to provide oxygen to users at either lower pressures or higher pressures. When providing low pressure oxygen, the disclosed oxygen concentrator may be used with a conventional, low pressure oxygen delivery device, such as an oxygen cannula or mask, that is configured to deliver oxygen at approximate source pressures of 5 psig to 8 psig. When providing high pressure oxygen, the disclosed oxygen concentrator may be used with a high pressure oxygen delivery device, such as a low profile nasal cannula, that is configured to deliver oxygen at approximate source pressures of 15 psig to 20 psig. The oxygen concentrator described below is also configured to automatically select whether low pressure oxygen or high pressure oxygen should be output to the user based on the type of connector used to couple a delivery device thereto, or based on characteristics of the delivery device itself.

Oxygen Concentrator with Multiple Output Pressures

Figure 1:
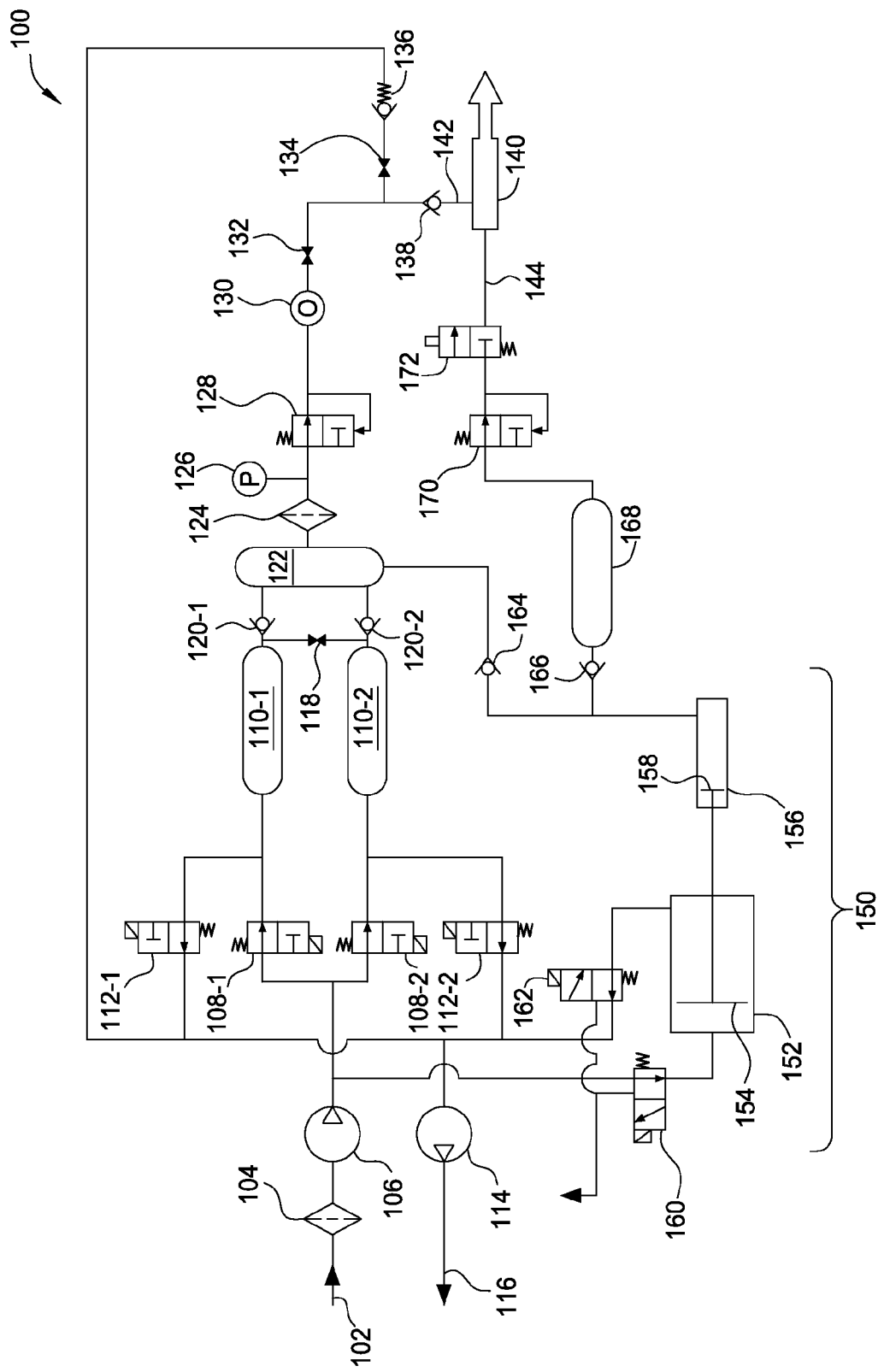
FIG. 1 illustrates an oxygen concentrator configured to implement one or more aspects of the present invention.

FIG. 1 illustrates an oxygen concentrator 100 configured to implement one or more aspects of the present invention. As shown, oxygen concentrator 100 includes an inlet port 102, an inlet filter 104, a compressor pump 106, sieve bed inlet valves 108-1 and 108-2, sieve beds 110-1 and 110-2, sieve bed dump valves 112-1 and 112-2, vacuum pump 114, exhaust port 116, equalization orifice 118, check valves 120-1 and 120-2, and product tank 122.

Inlet port 102 is coupled to inlet filter 104, which, in turn, is coupled to compressor pump 106. Compressor pump is coupled to sieve beds 110-1 and 110-2 via sieve bed inlet valves 108-1 and 108-2, respectively. Sieve beds 110-1 and 110-2 are coupled to vacuum pump 114 via sieve bed dump valves 112-1 and 112-2, respectively. Vacuum pump 114 is coupled to outlet port 116. Sieve beds 110 are also coupled together via equalization orifice 118. Sieve bed 110-1 is coupled to product tank 122 via check valve 120-1, and sieve bed 110-2 is likewise coupled to product tank 122 via check valve 120-2.

In operation, compressor pump 106 intakes air from the environment at an ambient pressure via inlet port 102 and inlet filter 104. Compressor pump 106 drives air into either of sieve beds 110 in an alternating fashion. The particular sieve bed 110 to which compressor pump 106 drives air depends on the state of sieve bed inlet valves 108. Sieve bed inlet valves 108 are configured to open and close in alternation with one another, so that one sieve bed inlet valve 108 is open when the other sieve bed inlet valve is closed. Accordingly, when sieve bed inlet valve 108-1 is open, sieve bed inlet valve 108-2 is closed, and compressor pump 106 drives compressed air into sieve bed 110-1. Likewise, when sieve bed inlet valve 108-2 is open, sieve bed inlet valve 108-1 is closed, and compressor pump 106 drives compressed air into sieve bed 110-2.

Sieve beds 110 include a zeolitic substance that adsorbs nitrogen. When compressor pump 106 drives compressed air into one of sieve beds 110, the zeolitic substance within that sieve bed attracts nitrogen molecules without substantially attracting oxygen molecules. Thus, when compressor pump 106 drives compressed air into a particular sieve bed 110, that sieve bed retains nitrogen while permitting oxygen to escape into product tank 122 via the associated check valve 120. Since the nitrogen adsorption process requires a certain non-zero amount of time to occur, sieve beds 110 are configured to operate in parallel with one another, in an alternating fashion that depends on the alternation of sieve bed inlet valves 108, thereby doubling oxygen throughput to product tank 122.

In conjunction with compressor pump 106 driving air into sieve beds 110, vacuum pump 114 draws nitrogen out of sieve beds 110, in a similarly alternating fashion, for exhaust via exhaust port 116. The particular sieve bed 110 from which vacuum pump 114 draws nitrogen depends on the state of sieve bed dump valves 112. Sieve bed dump valves 112 are configured to open and close in alternation with one another, so that one sieve bed dump valve 112 is open when the other sieve bed dump valve 112 is closed. Accordingly, when sieve bed dump valve 112-1 is open, sieve bed dump valve 112-2 is closed, and vacuum pump 114 draws nitrogen out of sieve bed 110-1 for exhaust. Likewise, when sieve bed dump valve 112-2 is open, sieve bed dump valve 112-1 is closed, and vacuum pump 114 draws nitrogen out of sieve bed 110-2 for exhaust. Drawing nitrogen out of sieve beds 110 in this fashion removes nitrogen molecules from the zeolitic substance within those sieve beds 110 and readies that substance for subsequent nitrogen adsorption.

Sieve bed dump valves 112 are configured to open and close in synchronized alternation with the closing and opening of sieve bed inlet valves 108, so that one sieve bed dump valve 112 is open when the corresponding sieve bed inlet valve 108 is closed, and vice versa. Accordingly, sieve bed dump valve 112-1 is open when sieve bed inlet valve 108-1 is closed. Likewise, sieve bed dump valve 112-2 is open when sieve bed inlet valve 108-2 is closed. In this manner, compressor pump 106 drives air into one of the sieve beds 110 while vacuum pump 114 removes nitrogen from the other sieve bed 110.

With the above configuration, in a first cycle, compressor pump 106 drives compressed air into sieve bed 110-1. Sieve bed inlet valve is 108-1 open and sieve bed dump valve 112-1 is closed. Sieve bed 110-1 scrubs nitrogen from the air driven therein and delivers oxygen to product tank 122. Simultaneously, vacuum pump 114 draws nitrogen (adsorbed during a previous cycle) from sieve bed 110-2 for exhaust via exhaust port 116. Sieve bed inlet valve 108-2 is closed and sieve bed dump valve 112-2 is open.

In a second cycle, compressor pump 106 drives compressed air into sieve bed 110-2. Sieve bed inlet valve is 108-2 open and sieve bed dump valve 112-2 is closed. Sieve bed 110-2 scrubs nitrogen from the air driven therein and delivers oxygen to product tank 122. Simultaneously, vacuum pump 114 draws nitrogen (adsorbed during the previous cycle) from sieve bed 110-1 for exhaust via exhaust port 116. Sieve bed inlet valve 108-1 is closed and sieve bed dump valve 112-1 is open. The two cycles described above repeat, in alternating fashion, thereby continuously delivering oxygen to product tank 122 while continuously exhausting nitrogen via exhaust port 116.

As also shown, product tank 122 is coupled via a product filter 124 to a pressure sensor 126, which, in turn, is coupled to a pressure regulator 128. Pressure regulator 128 is coupled to an oxygen sensor 130 and to a user flow control orifice 132. User flow control orifice is coupled via a check valve 138 to user connection switch 140. The user of oxygen concentrator 100 may connect an oxygen delivery device, such as an oxygen mask, a nasal cannula, and so forth, to user connection switch 140. The user may then adjust the flow of oxygen by manipulating user flow control orifice 132.

In one embodiment, oxygen sensor 130 is coupled downstream to vacuum pump 114 via bleed orifice 134 and spring-loaded pressure relief valve 136. In this embodiment, the accuracy of oxygen sensor 130 may depend on the flow rate of oxygen form product tank 122. Accordingly, bleed orifice 134 and spring-loaded pressure relief valve 136 allow a small amount of oxygen to bleed out to vacuum pump 114, thereby maintaining the needed flow of oxygen. Persons skilled in the art will recognize that the configuration described in this embodiment may only be implemented when the accuracy of oxygen sensor 130 substantially depends on the flow of oxygen.

When user flow control orifice 132 is open, oxygen flows from product tank 122, through product filter 124, to pressure sensor 126 and pressure regulator 128. Pressure sensor 126 detects the pressure associated with the flowing oxygen.

Pressure regulator 128 regulates that pressure to approximately 5 psig. Oxygen sensor 130 verifies the oxygen concentration prior to delivery to the user via user connection switch 140.

User connection switch 140 is thus configured to deliver low pressure oxygen from low pressure oxygen outlet 142 to the user. In the context of the present disclosure, "low pressure" may refer to an approximate pressure of 5 psig to 8 psig. User connection switch 140 is also configured to deliver high pressure oxygen from high pressure oxygen outlet 144 to the user via user connection switch 140. In the context of this disclosure, "high pressure" may refer to an approximate pressure of 15 to 50 psig. User connection switch 140 is configured to output only low-pressure oxygen or, alternatively, both low pressure oxygen and high pressure oxygen, depending on the connector coupled thereto or the delivery device coupled thereto.

In one embodiment, user connection switch 140 may be a mechanical device configured to select specific pressures of oxygen for output depending on a mechanical connector coupled thereto. As described in greater detail below in conjunction with FIGS. 2A-2C, the user of the oxygen concentrator may couple a proprietary connector to user connection switch 140 that selects between low pressure oxygen outlet 142 and high pressure oxygen outlet 144 or selects both of those outlets together. Alternatively, the user could couple a non-proprietary connection to user connection switch 140 and, in response, user connection switch 140 selects only low pressure oxygen outlet 142.

In another embodiment user connection switch 140 may be a pneumatic device configured to select specific pressures of oxygen for output depending on a delivery device coupled thereto. As described in greater detail below in conjunction with FIGS. 3A-3B, the user of oxygen concentrator may couple a delivery device to user connection device 140 that is configured to deliver oxygen at a high pressure to an oxygen delivery device and, thus create a relatively high backpressure. In response to this higher backpressure, user connection switch 140 selects high pressure oxygen outlet 144, or selects both low pressure oxygen outlet 142 and high pressure oxygen outlet 144, for connection to the high pressure delivery device. Alternatively, the user of oxygen concentrator may couple a delivery device to user connection device 140 that is configured to deliver oxygen at a low pressure to the user and, thus, induce a relatively low backpressure. In response to this lower backpressure, user connection switch 140 selects only low pressure oxygen outlet 142 for connection to the low pressure delivery device.

Oxygen concentrator 100 is configured to generate high pressure oxygen 144 using a pressure amplifier 150. As shown, pressure amplifier 150 includes a master cylinder 152 that includes a master piston 154 and a slave cylinder 156 that includes a slave piston 158. Master piston 154 is coupled to slave piston 158. Master cylinder 154 generally has a larger cross-sectional area compared to slave cylinder 158, for reasons discussed in greater detail below.

Master cylinder 152 is coupled to compressor pump 106 via positive pressure valve 160 and to vacuum pump 114 via negative pressure valve 162. Specifically, compressor pump 106 is coupled to a first region of master cylinder 152 residing to the left hand side of master piston 154, and vacuum pump 114 is coupled to a second region of master cylinder residing to the right hand side of master piston 154. Slave cylinder 156 is coupled to product tank 122 via check valve 164. Specifically, product tank 122 is coupled to a region of slave cylinder 156 to the right hand side of slave piston 158. Accordingly, the right hand region of slave cylinder 156 may be flooded with pressurized oxygen from product tank 122. Slave cylinder 156 is also coupled via check valve 166 to high pressure product tank 168.

Positive pressure valve 160 and negative pressure valve 162 are configured to open and close periodically, and in synchrony with one another, in order to periodically drive master piston 152 to the right. When positive pressure valve 160 and negative pressure valve 162 are open (as shown), master piston 154 is subject to a pressure differential that depends on the difference between the positive pressure induced by compressor pump 106 within the left hand region of master cylinder 152 and the negative pressure induced by vacuum pump 114 within the right hand region of master cylinder 152. This pressure differential exerts a force on master piston 154 that is proportional to the cross-sectional area of master piston 154. Master piston 154 transfers that force to slave piston 158 periodically, when positive pressure valve 160 and negative pressure valve 162 are both open.

Slave piston 158 is subject to the periodic force received from master piston 154 and also subject to a pressure force exerted by the pressurized oxygen received from product tank 122. However, the periodic force received from master piston 154 is typically greater than the pressure force exerted by the pressurized oxygen for at least two reasons. First, the pressure differential between the positive pressure associated with compressor pump 106 and the negative pressure associated with vacuum pump 114 is typically greater than the pressure associated with the pressurized oxygen within slave cylinder 156, and so master piston 154 and slave piston 158 alike are subject to a force imbalance that drives those pistons to the right. Secondly, because the cross-sectional area of master piston 154 exceeds that of slave piston 158, the force exerted on master piston 154 for a given pressure is greater than that exerted on slave piston 158 for that same pressure. For these reasons, the difference in cross-sectional areas between master cylinder 154 and slave cylinder 158 amplifies the existing pressure imbalance between those two cylinders, thereby inducing a substantial force.

Thus, when positive pressure valve 160 and negative pressure valve 162 are both open, slave cylinder 156 is driven to the right, thereby further compressing the pressurized oxygen within the right hand region of slave cylinder 156 and forcing the resultant high pressure oxygen into high pressure product tank 168. Check valve 164 prevents the backflow of high pressure oxygen into product tank 122, which has a comparatively lower pressure.

When positive pressure valve 160 and negative pressure valve 162 are subsequently closed (venting both sides of the master cylinder to atmosphere), the pressurized oxygen from product tank 122 forces slave piston 158 to the left, thereby returning master piston 154 to the left. Check valve 166 prevents the escape of high pressure oxygen from product tank 168.

The cycle described above repeats, thereby pressurizing oxygen received from product tank 122 and storing that high pressure oxygen in product tank 168. Product tank 168 is coupled downstream to a pressure regulator 170 that is configured to regulate the pressure of the oxygen stored therein to approximately 20 psig. High pressure oxygen is thus provided to user connection switch 140, in addition to low pressure oxygen.

In one embodiment, pressure amplifier 150 is configured to drive master cylinder 152 with the positive pressure provided by compressor pump 106 alone, without relying on the negative pressure provided by vacuum pump 114. This configuration may be applicable to stationary ventilators that do not include a vacuum pump. In such cases, the ratio between the cross-sectional area of master piston 154 and that of slave piston 158 may be adjusted to provide the appropriate pressure amplification.

By implementing the unique mechanical architecture described above, oxygen concentrator 100 is capable of delivering oxygen with lower pressures suitable for low pressure delivery devices, and, additionally, delivering oxygen with higher pressures suitable for high pressure delivery devices. Since oxygen concentrator 100 generates high pressure oxygen using the pressure differential that exists between compressor pump 106 and vacuum pump 114, oxygen concentrator 100 consumes a similar amount of power compared to conventional oxygen concentrators. Accordingly, oxygen concentrator 100 is suitable for portable implementations that depend on battery power.

Further, since user connection switch 140 is configured to select the appropriate oxygen flow path, the user of oxygen concentrator 100 need not be aware of which oxygen flow path is suitable for a particular delivery device. As mentioned previously, user connection switch 140 may be a mechanical switch configured to detect a proprietary connector indicating that high pressure oxygen should be supplied, as described below in conjunction with FIGS. 2A-2C, or a pneumatic switch configured to detect a level of backpressure indicating that high pressure oxygen should be supplied, as described in greater detail below in conjunction with FIGS. 3A-3B.

User Connection Switch for Selecting between Output Pressures

Figure 2A:
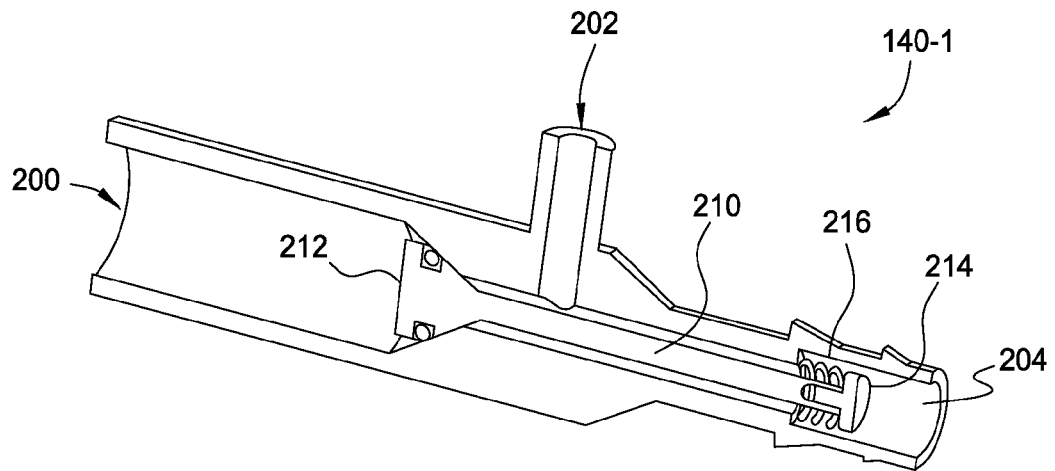
FIGS. 2A-2C illustrate various components associated with an exemplary mechanical connection switch that selects an oxygen flow path within the oxygen concentrator of FIG. 1, according to one embodiment of the present invention.

FIG. 2A illustrates an exemplary mechanical user connection switch 140-1 that selects an oxygen flow path within oxygen concentrator 100 of FIG. 1, according to one embodiment of the present invention. User connection switch 140-1 represents one exemplary embodiment of user connection switch 140 shown in FIG. 1. As mentioned above, an oxygen delivery device (not shown) may be coupled to user connection switch 140-1 in order to allow oxygen concentrator 100 to provide oxygen to a user. As discussed in greater detail below, various types of delivery devices may be coupled to user connection switch 140-1, using different types of connectors (not shown here), in order to allow either low pressure oxygen or high pressure oxygen to be provided to the user.

As shown, user connection switch 140-1 includes a high pressure oxygen inlet 200, a low pressure oxygen inlet 202, an oxygen outlet 204. User connection switch 140-1 also includes a spring-loaded flow path selector 210 that includes a valve 212, a valve pad 214, and a spring 216. Low pressure oxygen inlet 202 is nominally coupled to oxygen outlet 204. High pressure oxygen inlet 200 may be coupled to oxygen outlet 204, depending on whether valve 214 is open or closed.

In operation, spring 216 exerts a force against valve pad 214 that may cause flow path selector 210 to travel towards the right-hand side of user connection switch 140-1 until valve 212 reaches a left-hand mechanical limit associated with high pressure oxygen inlet 200. When valve 212 reaches the left-hand mechanical limit, valve 212 is closed, and high pressure oxygen inlet 200 is disconnected from oxygen outlet 204. When valve 212 is closed, only low pressure oxygen inlet 202 is coupled to oxygen outlet 204.

However, if a force is exerted against valve pad 214 that is sufficient to overcome the force exerted by spring 216, then flow path selector 210 may travel towards the left-hand side of user connection switch 140-1 until valve pad 214 reaches a right-hand mechanical limit associated with oxygen outlet 204. When valve pad 214 reaches the right-hand mechanical limit, valve 212 is open, and high pressure oxygen inlet 200 is connected to oxygen outlet 204 in tandem with low pressure oxygen inlet 202 being coupled thereto.

As a general matter, a conventional connector may be used in conjunction with a conventional delivery device that operates with low pressure oxygen. Such connectors may couple to user connection device 140-1 in a conventional fashion and lacks any mechanical means to exert force against valve pad 214. Consequently, a conventional connector may allow valve 212 to remain in the closed state, thereby only coupling low pressure oxygen inlet 202 to oxygen outlet 204 and only delivering low pressure oxygen to the low pressure delivery device, as desired.

Conversely, a proprietary connector may be used in conjunction with a delivery device that operates with high pressure oxygen. Such proprietary connectors may couple to user connection device 140-1 in a manner that exerts a force against valve pad 214 and, as a result, causes valve 212 to open. Accordingly, a proprietary connector may cause flow path selector 210 to couple high pressure oxygen inlet 200 to oxygen outlet 204, or to couple both high pressure oxygen inlet 200 and low pressure oxygen inlet 202 to oxygen outlet 204, thereby delivering high pressure oxygen to the high pressure delivery device, as desired. An example of a proprietary connector is described in greater detail below in conjunction with FIG. 2B.

Figure 2B:
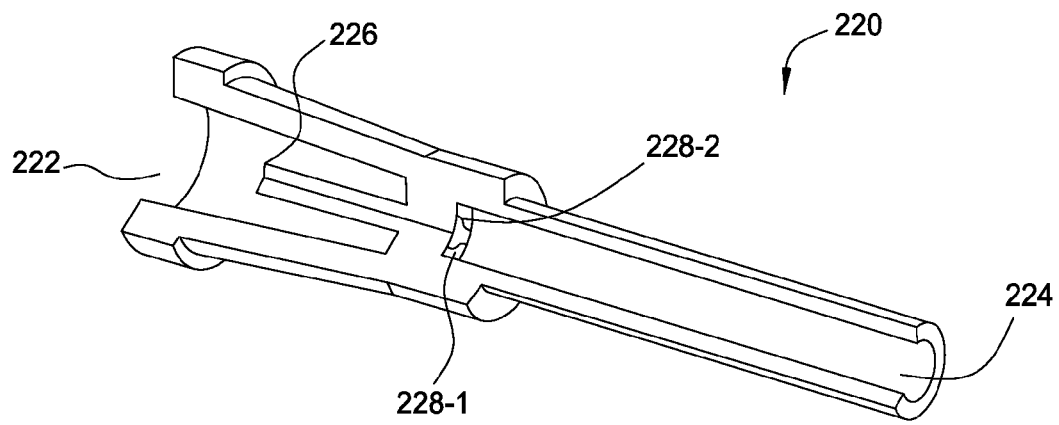

FIG. 2B illustrates a proprietary connector 220 that includes connection port 222 and a tubing port 224, according to one embodiment of the present invention. Connection port 222 may be coupled to oxygen outlet 204 of user connection switch 140-1 shown in FIG. 2A. Tubing port 224 may be coupled to tubing that, in turn, is coupled to a delivery device (not shown). Proprietary connector 220 also includes a valve depressor 226. When proprietary connector 220 is attached to user connection switch 140-1, valve depressor 226 exerts a force against valve pad 214, thereby causing flow path selector 210 to travel to the left-hand mechanical limit and opening valve 212. In the open state, valve 212 allows high pressure oxygen to flow through proprietary connector 220 to a delivery device. Valve depressor 226 includes various channels 228-1 and 228-2 that permit oxygen to flow through proprietary connector 220.

Figure 2C:
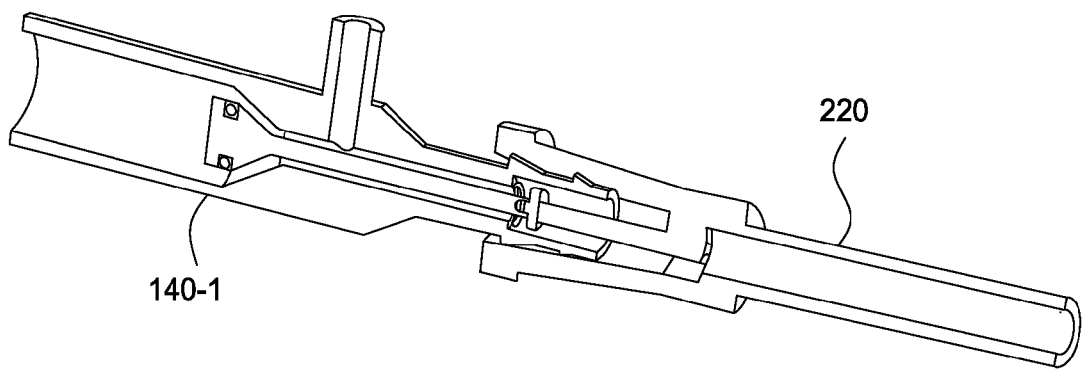

FIG. 2C illustrates user connection switch 140-1 within oxygen concentrator 100 of FIG. 1 coupled to proprietary connector 220, according to one embodiment of the present invention. As shown, valve 214 remains open so long as proprietary connector 220 is connected to user connection switch 140-1. When proprietary connector 200 is removed, flow path selector 210 returns to the right-hand mechanical limit and valve 214 closes, thereby terminating the flow of high pressure oxygen.

Figure 3A:
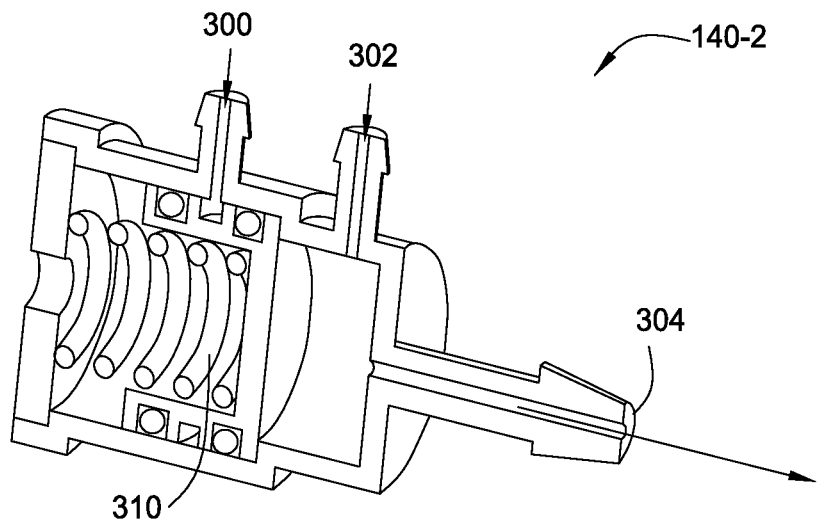
FIGS. 3A-3B illustrate an exemplary pneumatic connection switch that selects an oxygen flow path within the oxygen concentrator of FIG. 1, according to another embodiment of the present invention.
Figure 3B:
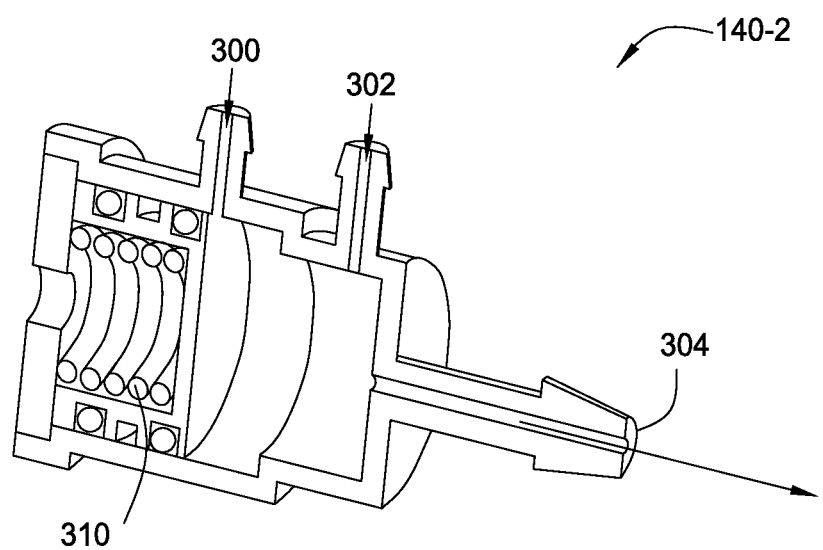

By implementing the techniques described above in conjunction with FIGS. 2A-2C, user connection switch 140-1 selects the appropriate pressure of oxygen based on the type of connector coupled thereto. This approach removes from the user the burden of selecting the correct oxygen pressure for a given type of delivery device, thereby improving usability of oxygen concentrator 100. FIGS. 3A-3B, described in greater detail below, illustrate another approach to selecting oxygen pressures.

FIG. 3A illustrates an exemplary pneumatic user connection switch 140-2 that selects an oxygen flow path within oxygen concentrator 100 of FIG. 1, according to another embodiment of the present invention. Pneumatic user connection switch 140-2 represents another exemplary embodiment of user connection switch 140 shown in FIG. 1. Like mechanical user connection switch 140-1 described above, various types of delivery devices may be coupled to user connection switch 140-2, using different types of connectors (not shown), in order to allow either low pressure oxygen or high pressure oxygen to be provided to the user. In particular, low pressure delivery devices that operate with low oxygen pressures may be coupled to user connection switch 140-2, as well as high pressure delivery devices that operate with high oxygen pressures.

As shown, pneumatic user connection switch 140-2 includes a high pressure oxygen inlet 300, a low pressure oxygen inlet 302, an oxygen outlet 304, and a spring-loaded piston 310. Piston 310 exerts a force towards the right-hand side of user connection switch 140-1, and may therefore travel towards a right-hand mechanical limit associated with user connection switch 140-1. At the right hand mechanical limit, piston 310 disconnects high pressure oxygen inlet 300 from oxygen outlet 304 while allowing low pressure oxygen inlet 302 to remain connected to oxygen outlet 304.

Piston 310 generally assumes the position shown in FIG. 3A when a conventional, low pressure delivery device is coupled to user connection switch 140-2. As known in the art, delivery devices induce a backpressure that is proportional to the pressure of oxygen delivered to the user. With low pressure delivery devices, a relatively low backpressure is induced which exerts a concordantly weak counterforce against piston 310. That counterforce is generally insufficient to cause the spring-loaded piston 310 to travel, and so oxygen outlet 304 remains connected only to low pressure oxygen inlet 304. However, a high pressure delivery device may induce a greater backpressure that does, in fact, cause piston 310 to travel, as shown in FIG. 3B.

FIG. 3B illustrates user connection switch 140-2 within oxygen concentrator 100 of FIG. 1 when coupled to a high pressure delivery device (not shown), according to one embodiment of the present invention. As mentioned above, a high pressure delivery device may induce a backpressure within user connection device 140-2 sufficient to overcome the force exerted by piston 310, thereby causing piston 310 to travel. As shown, piston 310 travels to the left-hand mechanical limit of user connection device 140-1, thereby coupling high pressure oxygen inlet 300 to oxygen outlet 304 as well as coupling low pressure oxygen inlet 302 to oxygen outlet 304. In one embodiment, in the configuration shown in FIG. 3B, low pressure oxygen inlet 302 is disconnected from oxygen outlet 304.

Persons skilled in the art will recognize that a threshold amount of backpressure may be needed to cause piston 310 to travel sufficiently to the left in order to couple high pressure oxygen inlet 300 to oxygen outlet 304. The threshold amount of backpressure may depend on a spring constant associated with piston 310 and the amount of travel needed to expose high pressure oxygen inlet 300. Those skilled in the art will understand that derivation of the aforesaid threshold backpressure is a simple matter of applying Hooke's Law to the specific geometry associated with user connection switch 140-2.

By implementing the techniques described above in conjunction with FIGS. 3A-3B, user connection switch 140-2 selects the appropriate pressure of oxygen based on the type of delivery device coupled thereto, without needing a specific connector type. This approach removes from the user the burden of selecting the correct oxygen pressure for a given type of delivery device and also obviates the need for a special, proprietary connector.

Referring generally to FIGS. 1-3B, the various techniques described thus far enable users to obtain oxygen at a range of different pressures corresponding to different types of oxygen delivery devices. Accordingly, the user may rely upon conventional low pressure delivery devices or, alternatively, high pressure oxygen delivery devices, depending on user preference. In addition, the user is not required to perform any special configurations to enable low pressure oxygen versus high pressure oxygen; the user need only attach the preferred oxygen delivery device, and the correct oxygen pressure is automatically selected. The various techniques described above are also described in stepwise fashion below in conjunction with FIGS. 4-6.

Techniques for Delivering Oxygen to a User

Figure 4:
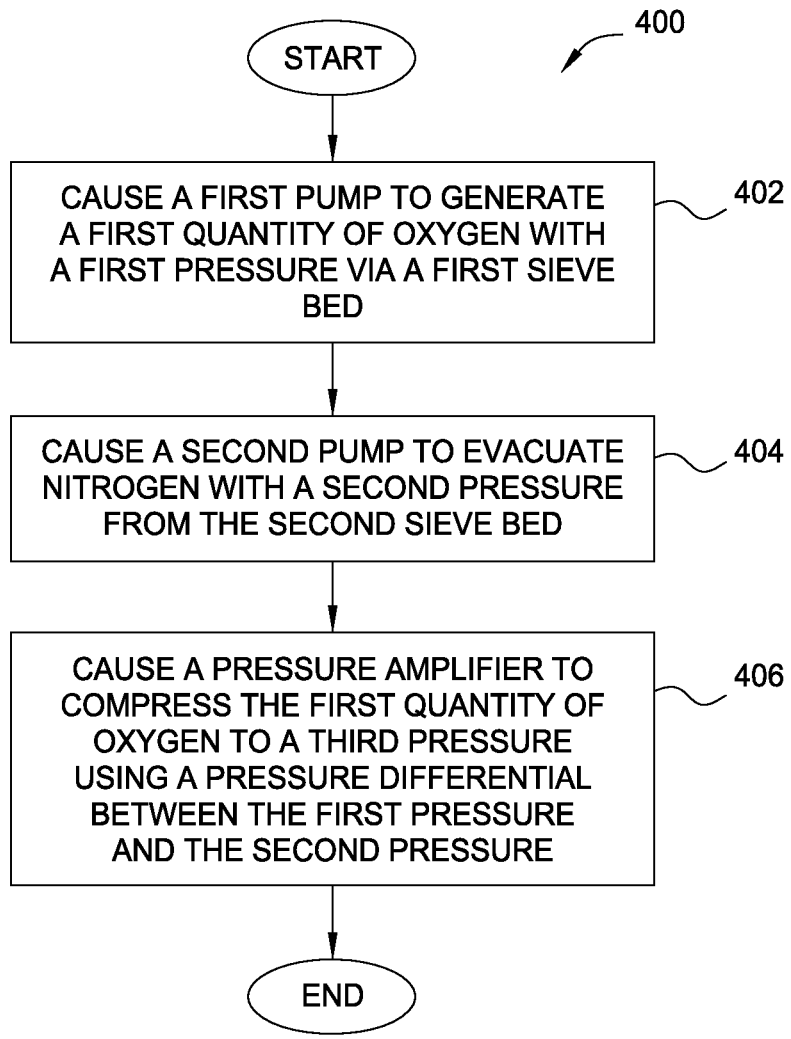
FIG. 4 is a flow diagram of method steps for pressurizing oxygen within an oxygen concentrator, according to one embodiment of the present invention.

FIG. 4 is a flow diagram of method steps for pressurizing oxygen within an oxygen concentrator, according to one embodiment of the present invention. Although the method steps are described in conjunction with the systems of FIGS. 1-3B, persons skilled in the art will understand that any system configured to perform the method steps, in any order, is within the scope of the present invention.

As shown, a method 400 begins at step 402, where a first pump within oxygen concentrator 100 generates a first quantity of oxygen with a first pressure via a first sieve bed. For example, compressor pump 106 could generate the first quantity of oxygen with the first pressure via sieve bed 110-1. The first quantity of oxygen is stored in product tank 122.

At step 404, a second pump within oxygen concentrator 100 evacuates nitrogen with a second pressure from a second sieve bed. For example, vacuum pump 114 could evacuate nitrogen from sieve bed 110-2. The nitrogen is generally evacuated into the environment via exhaust port 116.

At step 406, a pressure amplifier within oxygen concentrator 100 compresses the first quantity of oxygen to a third pressure using a pressure differential between the first pressure and the second pressure. For example, pressure amplifier 150 could drive master cylinder 152 with the pressure differential between compressor pump 106 and vacuum pump 114, thereby causing slave cylinder 156 to compress oxygen from product tank 122 into high pressure product tank 168. The method 400 then ends.

Steps 402 and 404 of the method 400 may be repeated continuously and in alternation between sieve beds 110-1 and 110-2, in conjunction with the alternation between sieve bed inlet valves 108-1 and 108-2 and sieve bed dump valves 112-1 and 112-2. In addition, step 406 of the method 400 may be repeated continuously based on the frequency with which positive pressure valve 160 and negative pressure valve 162 open and close.

By implementing the method 400, oxygen concentrator 100 extracts work from the pressure differential between compressor pump 106 and vacuum pump 114, thereby harvesting energy that would otherwise be wasted. In doing so, oxygen concentrator 100 may provide oxygen at higher pressures without requiring a substantial increase in power consumption. Accordingly, oxygen concentrator 100 may be more easily implemented as portable device.

A user may couple a low pressure delivery device to oxygen concentrator 100 or a high pressure delivery device.

Figure 5:
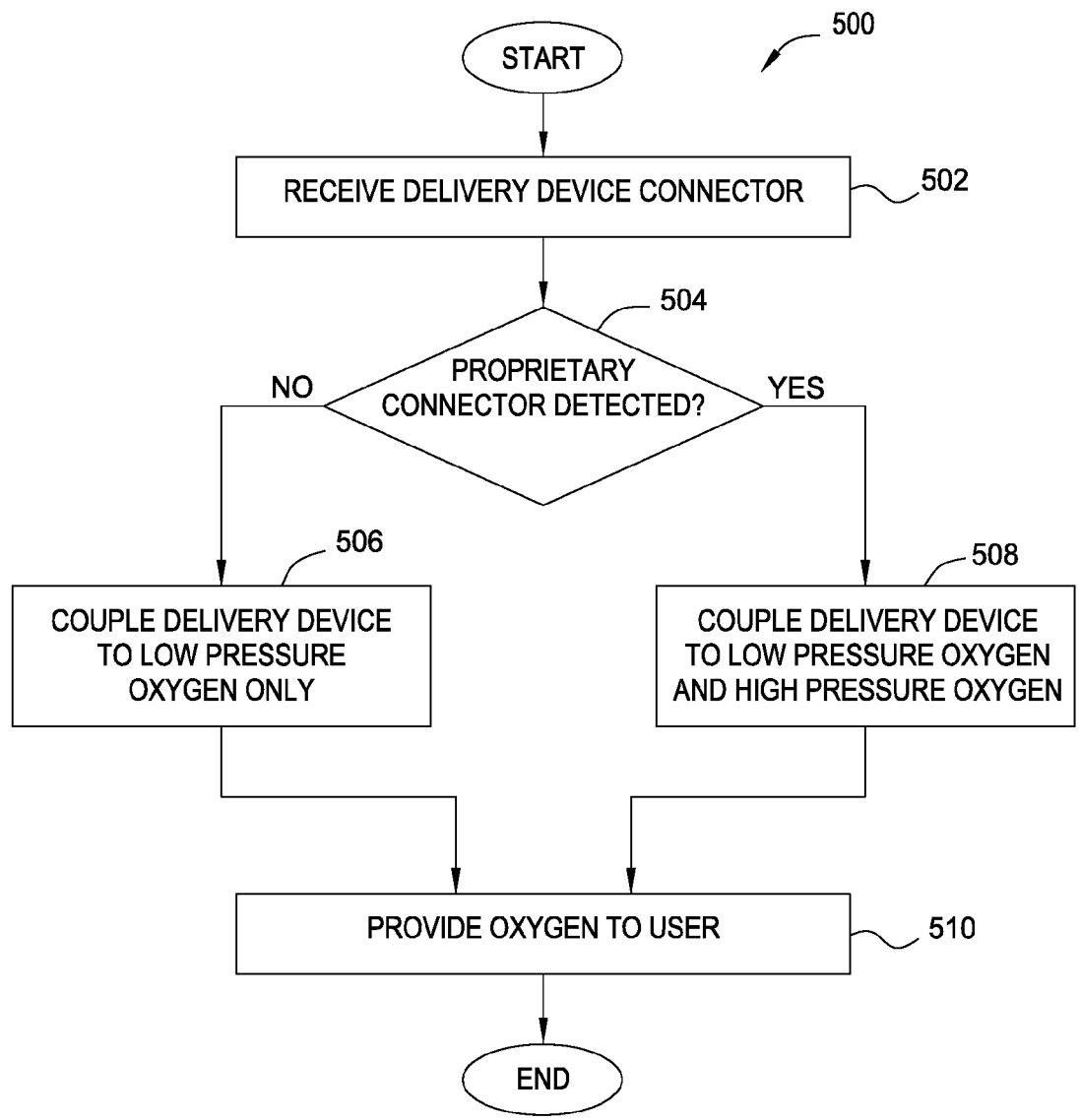
FIG. 5 is a flow diagram of method steps for delivering low pressure oxygen or high pressure oxygen from an oxygen concentrator to a user, according to one embodiment of the present invention.
Figure 6:
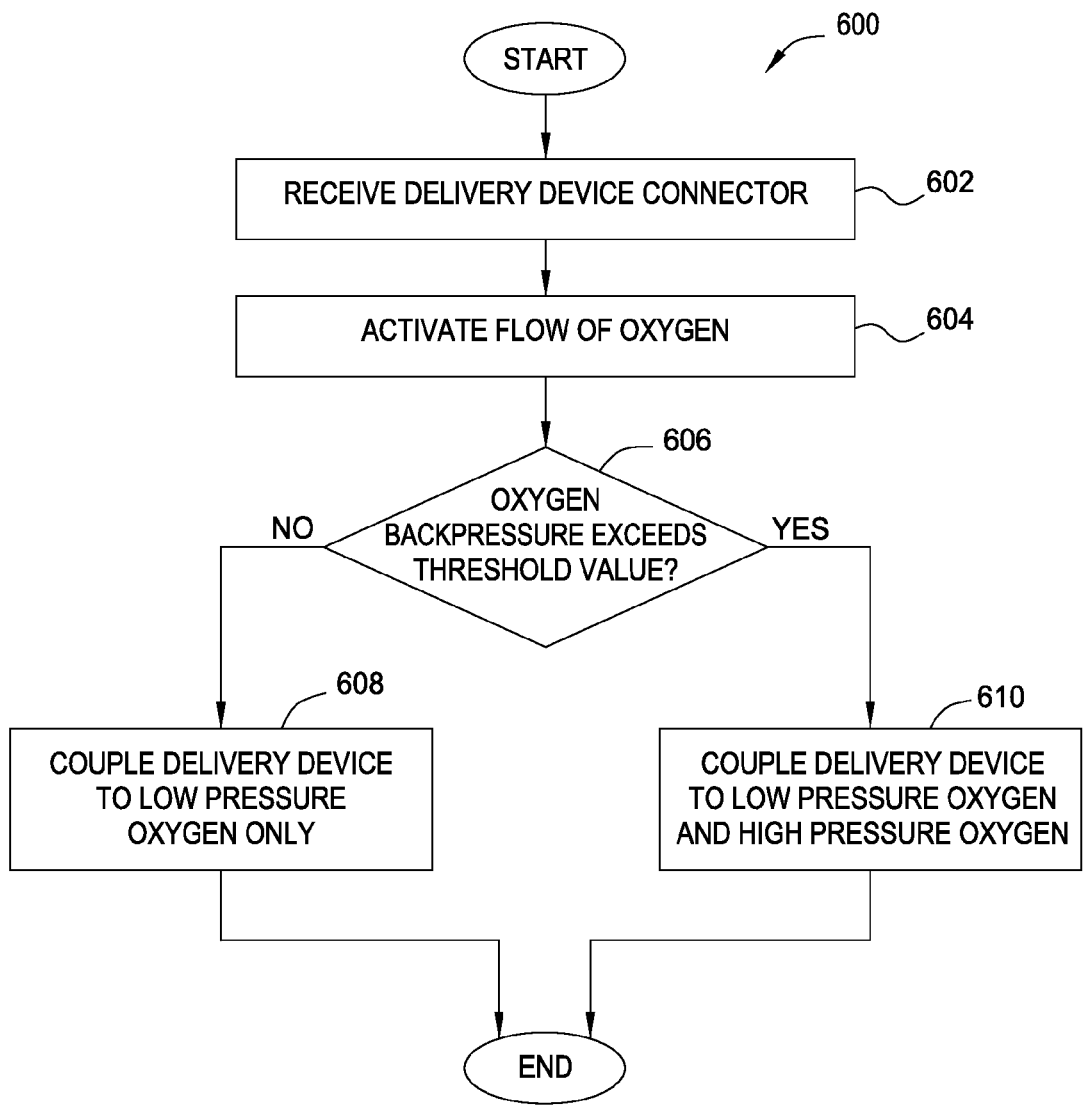
FIG. 6 is a flow diagram of method steps for delivering low pressure oxygen or high pressure oxygen from an oxygen concentrator to a user, according to another embodiment of the present invention.

Oxygen concentrator may include different versions of user connection switch 140, each configured to select the appropriate pressure of oxygen to be delivered to the delivery device. FIGS. 5-6 describe the operation of these different versions of user connection switch 140 in stepwise fashion.

FIG. 5 is a flow diagram of method steps for delivering low pressure oxygen or high pressure oxygen from an oxygen concentrator, according to one embodiment of the present invention. Although the method steps are described in conjunction with the systems of FIGS. 1-3B, persons skilled in the art will understand that any system configured to perform the method steps, in any order, is within the scope of the present invention.

As shown, a method 500 begins at step 502, where user connection switch 140-1 within oxygen concentrator 100 receives a delivery device connector. The delivery device connector could be a conventional connector, or a proprietary connector such as connector 220 shown in FIG. 2B.

At step 504, if a proprietary connector has not been coupled to user connection switch 140-1, then the method 500 proceeds to step 506. At step 506, user connection switch 140-1 couples the delivery device to low pressure oxygen inlet 202 only. In this configuration, low path selector 210 is positioned at the right-hand mechanical limit, and valve 212 remains closed. The method then proceeds to step 510, where oxygen is delivered to the user at the pressure selected by user connection switch 140-1 (in this case, a low pressure).

Returning to step 504, if a proprietary connector has been coupled to user connection switch 140-1, then the method 500 proceeds to step 508. At step 508, user connection switch 140-1 couples the delivery device to low pressure oxygen inlet 202 as well as to high pressure oxygen inlet 200. In one embodiment, at step 508 user connection switch 140-1 isolates the delivery device from low pressure oxygen inlet 202 while coupling that device to high-pressure oxygen inlet 200. In this configuration, valve depressor 226 causes flow path selector 210 to travel to the left-hand mechanical limit, and valve 212 opens. The method then proceeds to step 510, where oxygen is delivered to the user at the pressure selected by user connection switch 140-1 (in this case, a high pressure). The method 500 then ends.

By performing the steps of the method 500, user connection switch 140-1 is capable of selecting the appropriate pressure of oxygen for use with different delivery devices based on whether a proprietary connector is used. For example, a conventional low pressure delivery device such as an oxygen mask would not include a proprietary connector, and so user connection switch 140-1 would deliver the appropriately low pressure of oxygen to that mask. Conversely, a high pressure delivery device such as a low profile nasal cannula could include the proprietary connection, and so user connection switch 140-1 would deliver the appropriately high pressure of oxygen to that nasal cannula.

FIG. 6 is a flow diagram of method steps for delivering low pressure oxygen or high pressure oxygen from an oxygen concentrator, according to another embodiment of the present invention. Although the method steps are described in conjunction with the systems of FIGS. 1-3B, persons skilled in the art will understand that any system configured to perform the method steps, in any order, is within the scope of the present invention.

As shown, a method 600 begins at step 602, where user connection switch 140-2 within oxygen concentrator 100 receives a delivery device connector. The delivery device connector could be any type of connector. The delivery device may be a conventional low pressure delivery device, such as an oxygen mask, or a high pressure delivery device, such as a low profile nasal cannula.

At step 604 user flow control orifice 132 within oxygen concentrator 100 activates the flow of oxygen based on user input. User flow control orifice is typically a knob that controls the flow rate of oxygen delivered by oxygen concentrator 100. When the flow of oxygen is activated, the delivery device coupled to oxygen concentrator 100 induces a certain amount of backpressure depending on the type of device used. The backpressure may or may not exceed a threshold value, where that threshold depends on a spring constant associated with piston 310 and the amount of travel needed to expose high pressure oxygen inlet 300, as also described above in conjunction with FIG. 3B.

At step 606, if the induced backpressure does not exceed the threshold value, then the method 600 proceeds to step 608. At step 608, user connection switch 140-1 couples the delivery device only to low pressure oxygen. In this configuration, piston 310 remains sufficiently to the right-hand side of user connection switch 140-2 to block high pressure oxygen inlet 300 from connecting to oxygen outlet 304.

At step 606, if the induced backpressure does exceed the threshold value, then the method 600 proceeds to step 610. At step 610, user connection switch 140-1 couples the delivery device to both low pressure oxygen and high pressure oxygen. In one embodiment, at step 610 user connection switch 140-2 isolates the delivery device from low pressure oxygen while coupling that device to high pressure oxygen. In this configuration, piston 310 travels sufficiently to the left-hand side of user connection switch 140-2 to allow high pressure oxygen inlet 300 to couple to oxygen outlet 304. The method 600 then ends.

By performing the steps of the method 600, user connection switch 140-2 is capable of selecting the appropriate pressure of oxygen for use with different delivery devices based solely on the type of delivery device coupled thereto and the corresponding amount of backpressure induced by that device, without regard for the specific connector used. For example, a conventional low pressure delivery device such as an oxygen mask would induce a low backpressure, and so user connection switch 140-2 would deliver the appropriately low pressure of oxygen to that mask. Conversely, a high pressure delivery device such as a low profile nasal cannula would induce a high backpressure, and so user connection switch 140-1 would deliver the appropriately high pressure of oxygen to that nasal cannula.

In sum, an oxygen concentrator is configured to provide oxygen at either lower pressures or higher pressures. When providing low pressure oxygen, the disclosed oxygen concentrator may be used with a conventional, low pressure oxygen delivery device, such as an oxygen mask, that is configured to deliver oxygen at approximate pressures of 5 psig to 8 psig. When providing high pressure oxygen, the disclosed oxygen concentrator may be used with a high pressure oxygen delivery device, such as a low profile nasal cannula, that is configured to deliver oxygen at approximate pressures of 20 psig. The disclosed oxygen concentrator is configured to automatically select whether low pressure oxygen or high pressure oxygen should be output to the user based on the type of connector used to couple a delivery device thereto, or based on characteristics of the delivery device itself.

One advantage of the techniques set forth herein is that users may obtain oxygen at a range of different pressures corresponding to different types of oxygen delivery devices. Accordingly, the user may rely upon conventional low pressure delivery devices or, alternatively, high pressure oxygen delivery devices, depending on user preference. Furthermore, since the disclosed oxygen concentrator generates high pressure oxygen using the existing pressure differential between a compressor pump and a vacuum pump, the oxygen concentrator consumes an amount of power comparable to that consumed by conventional oxygen concentrators. Accordingly, the disclosed oxygen concentrator is suitable for portable implementations that depend on battery power.

Another advantage of the disclosed techniques is that the user of the oxygen concentrator need not be aware of which oxygen flow path is suitable for a particular device, because the user connection switch associated with the disclosed oxygen concentrator is configured to select the appropriate oxygen flow path. The user need only connect the preferred delivery device in order to receive the correct pressure of oxygen for that device.

While the foregoing is directed to embodiments of the present invention, other and further embodiments of the invention may be devised without departing from the basic scope thereof, and the scope thereof is determined by the claims that follow.

The invention claimed is:

1. A system for delivering oxygen to a user, the system comprising:
an oxygen concentrator that includes:
a first pump configured to pump atmospheric air through a first sieve bed at a first pressure to generate a first quantity of oxygen,
a second pump configured to evacuate nitrogen from a second sieve bed at a second pressure,
a pressure amplifier configured to pressurize the first quantity of oxygen to a third pressure to produce pressurized oxygen based on a pressure differential between the first pressure and the second pressure, and
a product tank coupled to the pressure amplifier and configured to store the pressurized oxygen for delivery to the user; and
a user connection switch, configured to deliver the pressurized oxygen to the user via a delivery device.

2. The system of claim 1, wherein the first pump comprises a compressor pump, and the first pressure has a positive value, and wherein the second pump comprises a vacuum pump, and the second pressure has a negative value.

3. The system of claim 1, wherein the pressure amplifier includes:
a first cylinder that includes a first piston;
a second cylinder that includes a second piston that is coupled to the first piston;
a first valve coupled to the first pump and to a first region of the first cylinder; and
a second valve coupled to the second pump and to a second region of the first cylinder.

4. The system of claim 3, wherein when the first valve is open the first region is subjected to the first pressure, and when the second valve is open the second region is subjected to the second pressure.

5. The system of claim 4, wherein the pressure differential between the first pressure and the second pressure exerts a force on the second piston via the first piston, causing the second piston to compress the first quantity of oxygen to the third pressure.

6. The system of claim 3, wherein the first piston has a first cross-sectional area, the second piston has a second cross-sectional area that is smaller than the first cross-sectional area.

7. The system of claim 6, wherein the third pressure is proportional to a ratio between the first cross-sectional area and the second cross-sectional area.

8. The system of claim 1, wherein the user connection switch is configured to deliver the pressurized oxygen to the user when a first connector is coupled to the user connection switch that opens a valve between the product tank and the delivery device.

9. The system of claim 1, wherein the user connection switch is configured to deliver the pressurized oxygen to the user when a first delivery device is coupled to the user connection switch that induces a backpressure that exceeds a threshold value.

10. The system of claim 1, wherein the delivery device comprises a low profile nasal cannula configured to deliver pressurized oxygen to the user having a pressure of at least 15 pounds per square inch gage (psig).

11. The system of claim 1, further comprising a low pressure product tank that is coupled to the first sieve bed and to the user connection switch and is configured to store the first quantity of oxygen at a fourth pressure that is less than the third pressure, wherein the user connection switch is configured to select, when connected to a high pressure delivery device that operates at a high pressure, a first oxygen flow path in the oxygen concentrator that connects the product tank to the high pressure delivery device, and to select, when connected to a low pressure delivery device that operates at a low pressure, a second oxygen flow path in the oxygen concentrator that connects the low pressure product tank to the low pressure delivery device.

12. An oxygen concentrator, comprising:
a first pump configured to pump atmospheric air through a first sieve bed at a first pressure to generate a first quantity of oxygen;
a second pump configured to evacuate nitrogen from a second sieve bed at a second pressure;
a pressure amplifier configured to pressurize the first quantity of oxygen to a third pressure to produce pressurized oxygen based on a pressure differential between the first pressure and the second pressure; and
a product tank coupled to the pressure amplifier and configured to store the pressurized oxygen for delivery to the user.

13. The oxygen concentrator of claim 12, wherein the first pump comprises a compressor pump, and the first pressure has a positive value, and wherein the second pump comprises a vacuum pump, and the second pressure has a negative value.

14. The oxygen concentrator of claim 12, wherein the pressure amplifier includes:
a first cylinder that includes a first piston;
a second cylinder that includes a second piston that is coupled to the first piston;
a first valve coupled to the first pump and to a first region of the first cylinder; and
a second valve coupled to the second pump and to a second region of the first cylinder.

15. The oxygen concentrator of claim 14, wherein when the first valve is open the first region is subjected to the first pressure, and when the second valve is open the second region is subjected to the second pressure, and wherein the pressure differential between the first pressure and the second pressure exerts a force on the second piston via the first piston, causing the second piston to compress the first quantity of oxygen to the third pressure.

16. The oxygen concentrator of claim 15, wherein when the first valve is closed and the second valve is closed, the first region and the second region are subjected to equal pressure, and the pressurized oxygen exerts a counterforce on the first piston via the second piston, causing the first piston to return to a first mechanical limit.

17. The oxygen concentrator of claim 15, wherein when the first valve is closed and the second valve is closed, the pressurized oxygen exerts a counterforce on the first piston via the second piston, causing the first piston to return to a first mechanical limit.

18. The oxygen concentrator of claim 14, wherein the first piston has a first cross-sectional area, the second piston has a second cross-sectional area that is smaller than the first cross-sectional area, and wherein the third pressure is proportional to a ratio between the first cross-sectional area and the second cross-sectional area.

19. The oxygen concentrator of claim 12, further comprising a user connection switch that is configured to deliver the pressurized oxygen to the user via a delivery device when a first connector is coupled to the user connection switch that opens a valve between the product tank and the delivery device.

20. The oxygen concentrator of claim 19, wherein the user connection switch is configured to deliver the pressurized oxygen to the user when a first delivery device is coupled to the user connection switch that induces a backpressure that exceeds a threshold value.

21. The oxygen concentrator of claim 19, wherein the delivery device comprises a low profile nasal cannula configured to deliver pressurized oxygen to the user having a pressure of at least 15 pounds per square inch gage (psig).

22. The oxygen concentrator of claim 12, further comprising:
a user connection switch configured to deliver the pressurized oxygen to the user via a delivery device; and
a low pressure product tank that is coupled to the first sieve bed and to the user connection switch and is configured to store the first quantity of oxygen at a fourth pressure that is less than the third pressure,
wherein the user connection switch is configured to select, when connected to a high pressure delivery device that operates at a high pressure, a first oxygen flow path in the oxygen concentrator that connects the product tank to the high pressure delivery device, and to select, when connected to a low pressure delivery device that operates at a low pressure, a second oxygen flow path in the oxygen concentrator that connects the low pressure product tank to the low pressure delivery device.

23. A method for compressing oxygen, the method comprising:
pumping atmospheric air with a first pump through a first sieve bed at a first pressure to generate a first quantity of oxygen;
evacuating nitrogen with a second pump from a second sieve bed at a second pressure;
pressurizing the first quantity of oxygen to a third pressure to produce pressurized oxygen based on a pressure differential between the first pressure and the second pressure; and
storing the pressurized oxygen for delivery to a user.

* * * * *